United States Patent
Ernst et al.

(10) Patent No.: US 6,365,740 B1
(45) Date of Patent: Apr. 2, 2002

(54) PREPARATION OF 2-METHYL-4-AMINO-5-AMINOMETHYLPYRIMIDINE

(75) Inventors: Hansgeorg Ernst, Speyer; Matthias Frauenkron, Ludwigshafen; Johann-Peter Melder, Böhl-Iggelheim; Frank Funke, Frankenthal; Andreas Keller, Germersheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/811,433

(22) Filed: Mar. 20, 2001

(30) Foreign Application Priority Data

Mar. 29, 2000 (DE) .......................................... 100 15 470

(51) Int. Cl.$^7$ ............................................ C07D 239/42
(52) U.S. Cl. ...................................................... 544/326
(58) Field of Search .......................................... 544/326

(56) References Cited

FOREIGN PATENT DOCUMENTS

DE 1 016 266 9/1957

OTHER PUBLICATIONS

Nishino et al. "The Reaction Mechanism of 2–Dimethoxymethyl–3–methoxypropionitrile with Acetamidine. I. A Revised Structure of the Intermediate" Bulletin of the Chemical Society of Japan, vol. 45, (1972) pp. 1127–1132.

Morimoto et al. "Bildungsmechanismus von 4–Amino–5–aminomethyl–2–methyl–pyrimidin aus 3–Athoxy–2–(diäthoxymethyl)propionitril und Acetamidin" Chemische Berichte vol. 106 (1973) pp. 893–901.

Ullmann's Encyklopädie der Technischen Chemie vol. 4, Band 17 pp. 330–332.

Ullmann's Encyclopedia of Industrial Chemistry vol. A27 pp. 515–517.

Rubtsov et al Chemical Abstract accession No. 1969:413139 for SU 237154.*

* cited by examiner

Primary Examiner—John M. Ford
(74) Attorney, Agent, or Firm—Keil & Weinkauf

(57) ABSTRACT

2-Methyl-4-amino-5-aminomethylpyrimidine of the formula 1

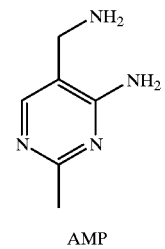

AMP is prepared by reacting 2-methyl-4-amino-5-alkoxymethylpyrimidine of the formula 2

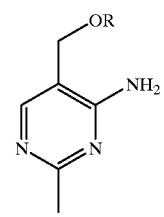

where R=$C_1$–$C_6$-alkyl, with ammonia in the presence of a catalyst.

21 Claims, No Drawings

PREPARATION OF 2-METHYL-4-AMINO-5-AMINOMETHYLPYRIDINE

The present invention relates to an improved process for preparing 2-methyl-4-amino-5-aminomethylpyrimidine of the formula 1 (hereinafter abbreviated as AMP),

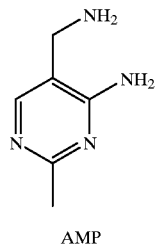

AMP starting from a 2-methyl-4-amino-5-alkoxy- methylpyrimidine of the formula 2,

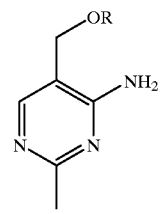

where
R is $C_1$–$C_6$ alkyl.

The derivative of the formula 2 in which R=methyl will hereinafter be referred to as MMP('methoxy-methylpyrimidine').

AMP 1 (formula 1) is the central intermediate in all industrially relevant processes for preparing vitamin B 1 (thiamine). Since the demand for this vitamin is continually increasing, many attempts have already been made to develop an advantageous process for preparing the pyrimidine part of thiamine.

An up-to-date and comprehensive review of these processes has appeared in, for example, Ullmann's Encyclopedia of Industrial Chemistry, Vol. A27 (1996), pp. 515–517. Starting materials used are generally acrylonitrile, malononitrile or acetonitrile.

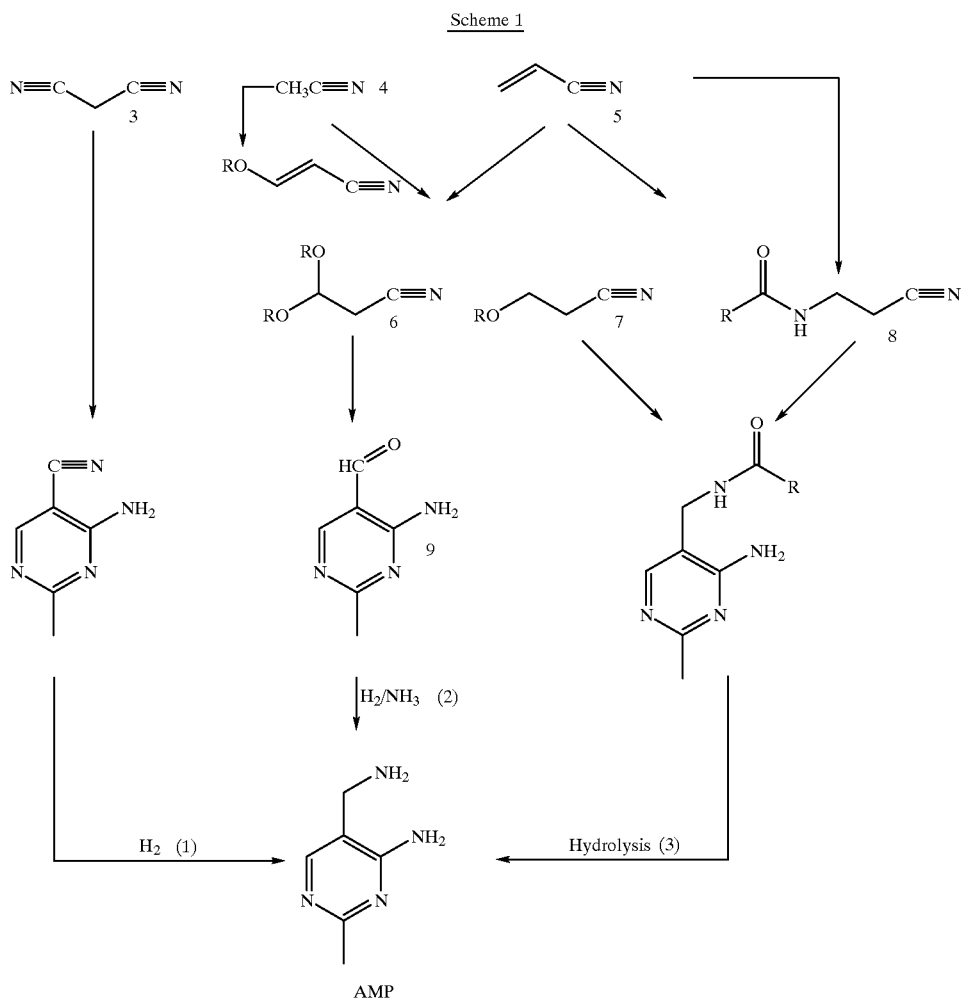

Scheme 1

In all these processes, the desired product AMP is not obtained directly, but rather the processes essentially give firstly AMP derivatives which are either in the wrong oxidation state or bear an N-acyl function. In all these processes, the aminomethyl side chain of AMP has to be generated by complicated and expensive reduction processes (hydrogenation of a nitrile group (1) or reductive amination of a formyl group (2)) or by hydrolysis of the N-acyl group (3).

Transformation of functional groups on valuable intermediates generally make a process cumbersome and thus uneconomical.

The known processes are also unfavorable in respect of the starting materials. Malononitrile 3 is very expensive and not unproblematical in terms of safety. The formation of the pyrimidine skeleton starting from acetonitrile 4 is time-consuming and cumbersome because of the additional process steps for introducing the $C_1$ building block. The synthetic routes from acrylonitrile 5 go via either β-dialkoxypropionitriles 6, N-functionalized β-aminopropionitriles 8 or β-alkoxypropionitriles 7.

The route via β-dialkoxypropionitrile 6 includes the abovementioned cumbersome reductive amination of a formylpyrimidine intermediate.

On the other hand, β-aminopropionitrile is not unproblematical in terms of safety and is also a very toxic substance. In contrast, β-alkoxypropionitriles are virtually nontoxic (Ullmann's Encyclopedie der technischen Chemie, 4th edition, volume 17 (1979), p. 330). The preparation of AMP from β-alkoxypropionitriles, which are readily handleable precursors because of their low toxicity, has been described repeatedly in the literature (cf., for example, Chem. Ber. 106 (1973), 893; Bull. Chem. Soc. Japan 45 (1972), 1127;DE-A 1016266).

A particularly disadvantageous aspect of the process carried out hitherto is that an additional equivalent of the expensive acetamidine is consumed for introduction of the aminomethylene nitrogen. The resulting N-acetyl-AMP has to be saponified under drastic conditions to form the free amine:

Furthermore, this process forms, as by-product, MMP which is not converted into AMP, thus adversely affecting the efficiency of the overall process.

In the literature, benzyl ethers of the type 2 have been subjected to various ether cleavages (Chim. Ther. 8 (1973) 1, 98; BE 590665;Khim.-Farm. Zh. 23 (1989), 11, 1374; U.S. Pat. No. 3,161,642; GB 953,875). These generally require drastic conditions (strong mineral acids).

The corresponding benzyl halide formed is reacted with $NH_3$ in a further step (Otkrytiya, Izobret., Prom. Obraztsy, Tovarnye Znaki 1969, 46 (8), 22). The selectivity of the monoalkylation of $NH_3$ with reactive halides is known to be poor. In view of the number and complexity of the steps, this process, too, is therefore very unfavorable.

It is an object of the present invention to develop a process which starts from the precursor β-alkoxypropionitrile and leads directly in a few simple steps to AMP without having the disadvantages of the prior art.

We have found that this object is achieved by converting 5-alkoxymethylpyrimidines of the formula 2, where R is $C_1$–$C_6$-alkyl, directly into AMP (1) with high selectivity by reaction with $NH_3$ in the presence of catalysts so as to replace the alkoxy radical.

Unless indicated otherwise, $C_1$–$C_6$-alkyl in the radical R is, either alone or in combination with, for example, alkoxy, a straight-chain, branched, saturated or unsaturated radical having 1–6 carbon atoms, e.g. a methyl, ethyl, propyl or isopropyl radical, preferably a methyl radical.

In the process of the present invention, 2 is initially charged in an inert organic solvent or in ammonia itself. Preferred solvents are aliphatic or aromatic organic solvents, for example cycloalkanes such as cyclohexane or decalin or else benzene, toluene, xylene or mesytilene. The solvents can be used either alone or in admixture with one another or with ammonia. 2 is preferably initially charged in ammonia itself.

After addition of the catalyst, the reaction is carried out in a temperature range of about 50–400° C., preferably about 180–350° C., particularly preferably in a range of 210–300° C.

Scheme 2

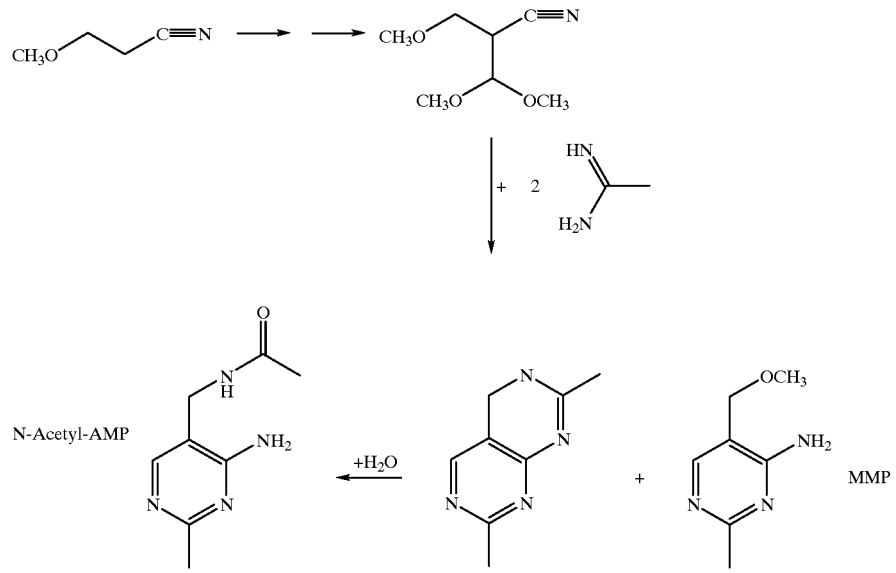

Catalysts used are Lewis or Bronsted acids, preferably Lewis-acid oxidic compounds of the elements of groups IV A and III B, particularly preferably $Al_2O_3$.

Ammonia is used in an amount of 1–500 equivalents, preferably 10–300 equivalents, particularly preferably 25–250 equivalents, per equivalent of 2.

Starting materials for the amination are 2-methyl-4-amino-5-alkoxymethylpyrimidines of the formula 2. The synthesis of 2 from the corresponding β-alkoxypropionitriles is described in the prior art (Pharm. Chem. J. 5 (1971), 8, 495; Khim.-Farm. Zh., 12 (1978), 7, 106).

For this purpose, the β-alkoxypropionitrile is firstly converted into the alkali metal enolate of the corresponding α-formyl-β-alkoxypropionitrile by condensation with a $C_1$–$C_6$-alkyl formate in the presence of an alkali metal alkoxide or by pressure reaction with carbon monoxide in a lower alkanol in the presence of an alkali metal alkoxide (DE-A 2107990). The α-formyl-β-alkoxypropionitrile is alkylated (e.g. using dimethyl sulfate: R"=$CH_3$) to give the corresponding enol ether. Condensation with acetamidine gives the 5-alkoxymethylpyrimidine of the formula 2 (see Scheme 3).

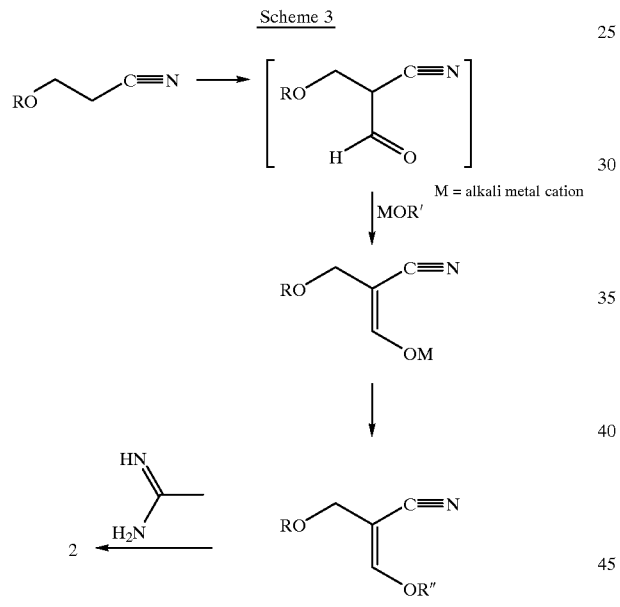

The process of the present invention for the direct conversion of 2 into AMP (1) thus provides a short and attractive route to this valuable vitamin B 1 precursor, starting from a favorable and readily handleable starting material.

The following examples illustrate the invention without restricting its scope.

EXAMPLE 1

1.25 g (8.2 mmol) of MMP and 5 g of $Al_2O_3$ (D-10-10, BASF) together with 50 ml of toluene were placed in a 300 ml autoclave. After closing the autoclave, 30 g (1.76 mol. 215 equivalents) of amonia were added and the mixture was heated at 230° C. for 4 hours stirring at the autogenous pressure. After cooling, the reaction mixture was filtered, taken up in ethanol and analyzed by gas chromatography (Table 1, Example 1).

EXAMPLES 2–9

1.25 g (8.2 mmol) of MMP and 5 g of catalyst together with 50 ml of toluene were placed in a 300 ml autoclave. After closing the autoclave, 30 g (1.76 mol, 215 equivalents) of ammonia were added and the mixture was heated for 4 hours while stirring at the autogenous pressure. After cooling, the reaction mixture was filtered, taken up in ethanol and analyzed by gas chromatography (Table 1).

TABLE 1

| Example | Catalyst | Temp. [° C.] | $NH_3$/MMP [mol/mol] | $C_{MMP}$ [%] | Yield of AMP [%] | Selectivity [%] |
|---|---|---|---|---|---|---|
| 1 | $Al_2O_3$ | 230 | 215 | 87 | 80 | 92 |
| 2 | $Al_2O_3$ | 230 | 55 | 45 | 39 | 87 |
| 3 | $Al_2O_3$ | 270 | 215 | 98 | 42 | 43 |
| 4 | $Al_2O_3$ | 210 | 215 | 40 | 34 | 86 |
| 5 | $H_3PO_4$ | 270 | 215 | 25 | 23 | 90 |
| 6 | $LaPO_4/TiO_2$ | 270 | 215 | 55 | 13 | 24 |
| 7 | $SiO_2$ | 230 | 215 | 2 | 1 | 50 |
| 8 | $TiO_2$ | 230 | 215 | 41 | 37 | 90 |
| 9 | $ZrO_2$ | 230 | 215 | 25 | 19 | 78 |

We claim:

1. A process for preparing 2-methyl-4-amino-5-aminomethylpyrimidine of the formula 1

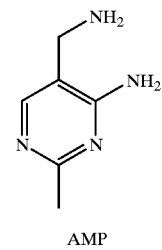

AMP by reacting 2-methyl-4-amino-5-alkoxymethylpyrimidine of the formula 2

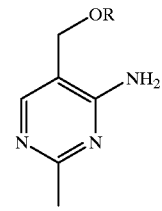

where R=$C_1$–$C_6$-alkyl, with ammonia in the presence of a catalyst.

2. A process as claimed in claim 1, wherein an inert, organic solvent is used as solvent.

3. A process as claimed in claim 1, wherein ammonia is used as solvent.

4. A process as claimed in claim 1, wherein the catalyst used is a Lewis or Brönsted acid.

5. A process as claimed in claim 1, wherein the catalyst used is a Lewis-acid oxide of an element of group IVA or IIIB.

6. A process as claimed in claim 1, wherein the catalyst used is $Al_2O_3$.

7. A process as claimed in claim 1, wherein the compound of the formula 2 is 2-methyl-4-amino-5-methoxymethylpyrimidine.

8. A process as claimed in claim 1, wherein after addition of the catalyst the reaction is carried out in a temperature range of 50–400° C.

9. A process as claimed in claim 1, wherein the catalyst used is selected from the group consisting of $Al_2O_3$, $H_3PO_4$, $LaPO_4/TiO_2$, $SiO_2$ and $ZrO_2$.

10. A process as claimed in claim 9, wherein the catalyst is selected from the group consisting of $Al_2O_3$, $H_3PO_4$, $LaPO_4/TiO_2$, $TiO_2$ and $ZrO_2$.

11. A process as claimed in 10, wherein the catalyst is $H_3PO_4$.

12. A process as claimed in claim 10, where the catalyst is $ZrO_2$.

13. A process as claimed in claim 1, wherein the molar ratio of ammonia to the compound of formula II is 1 to 500.

14. A process as claimed in claim 13, wherein said molar ratio is 25 to 250.

15. A process as claimed in claim 14, wherein said molar ratio is 55 to 215.

16. A process as claimed in claim 15, wherein said molar ratio is 215.

17. A process as claimed in claim 14, wherein the reaction is carried out in a temperature range of from 180 to 350° C.

18. The process of claim 4, wherein the molar ratio of ammonia to the compound of formula II is 25 to 250 and the reaction temperature is 180 to 350° C.

19. The process of claim 18, which is carried out in an inert organic solvent.

20. A process as claimed in claim 1, wherein the catalyst used is $Al_2O_3$, the molar ratio of ammonia to the compound of formula II is 25 to 250 and the reaction is carried out in a temperature range of 180 to 350° C.

21. The process of claim 20, which is carried out in an inert organic solvent.

* * * * *